(12) United States Patent
Rigler

(10) Patent No.: US 9,920,364 B2
(45) Date of Patent: Mar. 20, 2018

(54) CYCLIC SINGLE MOLECULE SEQUENCING PROCESS

(71) Applicant: Rudolf Rigler, Djursholm (SE)

(72) Inventor: Rudolf Rigler, Djursholm (SE)

(*) Notice: Subject to any disclaimer, the term of this patent is extended or adjusted under 35 U.S.C. 154(b) by 244 days.

(21) Appl. No.: 14/383,155

(22) PCT Filed: Mar. 5, 2013

(86) PCT No.: PCT/EP2013/054355
§ 371 (c)(1),
(2) Date: Sep. 5, 2014

(87) PCT Pub. No.: WO2013/131888
PCT Pub. Date: Sep. 12, 2013

(65) Prior Publication Data
US 2015/0080227 A1    Mar. 19, 2015

(30) Foreign Application Priority Data
Mar. 6, 2012    (EP) .................................... 12158246

(51) Int. Cl.
*C12Q 1/68* (2006.01)
*C07H 21/02* (2006.01)

(52) U.S. Cl.
CPC ......... *C12Q 1/6869* (2013.01); *C12Q 1/6874* (2013.01)

(58) Field of Classification Search
CPC ........ C12Q 2521/101; C12Q 2521/319; C12Q 2525/125; C12Q 2525/307; C12Q 2531/125; C12Q 2537/155; C12Q 2563/107; C12Q 2565/101; C12Q 1/6869; C12Q 2521/543; C12Q 2565/518
See application file for complete search history.

(56) References Cited

U.S. PATENT DOCUMENTS

| 7,033,764 | B2* | 4/2006 | Korlach ............... C12Q 1/6869 435/183 |
|---|---|---|---|
| 2004/0126780 | A1 | 7/2004 | Rigler et al. |
| 2004/0238756 | A1 | 12/2004 | Rigler et al. |
| 2005/0221375 | A1 | 10/2005 | Rigler et al. |
| 2007/0020626 | A1 | 1/2007 | Rigler et al. |
| 2007/0248966 | A1 | 10/2007 | Rigler et al. |
| 2010/0035269 | A1* | 2/2010 | Ma .......................... C12P 19/34 435/6.12 |
| 2010/0075328 | A1 | 3/2010 | Bjornson et al. |
| 2010/0260465 | A1* | 10/2010 | Hanzel .................... C12N 9/22 385/141 |
| 2011/0212437 | A1* | 9/2011 | Emig ..................... C07H 19/10 435/6.1 |

FOREIGN PATENT DOCUMENTS

| WO | 2006013110 A1 | 2/2006 |
| WO | 2010051773 A1 | 5/2010 |

OTHER PUBLICATIONS

Adessi, C. et al., Nucl. Acids Res., vol. 28, e87, pp. 1-8 (2000).*
Harris, T.D. et al., Science, vol. 320, pp. 106-109 (2008).*
Travers, K.J. et al., Nucl. Acids Res., vol. 38, e159, pp. 1-8 (2010).*
Eid, J. et al., Science, vol. 323, pp. 133-138 (2009).*
Maiden, M.C.J., Ann. Rev. Microbiol., vol. 60, pp. 561-588 (2006).*
International Search Report dated May 22, 2013 cited in PCT/EP2013/054355, 3 pgs.

* cited by examiner

*Primary Examiner* — Teresa E Strzelecka
(74) *Attorney, Agent, or Firm* — Rothwell, Figg, Ernst & Manbeck, P.C.

(57) ABSTRACT

The invention relates to a process for parallel high throughput sequencing of nucleic acid molecules, in particular in the single molecule format.

33 Claims, 7 Drawing Sheets

CYCLIC SINGLE MOLECULE SEQUENCING PROCESS

CROSS REFERENCE TO RELATED APPLICATION

Figure 1:
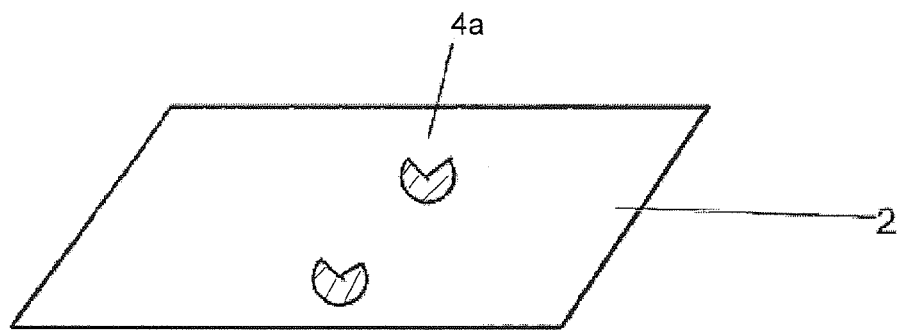

This application is a 35 U.S.C. 371 National Phase Entry Application from PCT/EP2013/054355, filed Mach 5, 2013, which claims the benefit of European Patent Application No. 12158246.4 filed on Mar. 6, 2012, the disclosure of which is incorporated herein in its entirety by reference.

The invention relates to a process for parallel high throughput sequencing of nucleic acid molecules, in particular in the single molecule format.

Sequencing of the human genome which consists of approx. $3 \times 10^9$ bases, or of the genome of other organisms and the determination and comparison of individual sequence variants requires the provision of sequencing methods which firstly are fast and secondly can be employed routinely and cost-effectively. Although large efforts have been made in order to accelerate familiar sequencing methods, for example the enzymic chain termination method according to Sanger et al. (Proc. Natl. Acad. Sci. USA 74 (1977) 5463), in particular by automation (Adams et al., Automated DNA Sequencing and Analysis (1994), New York, Academic Press), currently only up to 2000 bases per day can be determined using an automated sequencer.

Over recent years, new approaches to overcome the limitations of conventional sequencing methods have been developed, inter alia sequencing by scanning tunnelling microscopy (Lindsay and Phillip, Gen. Anal. Tech Appl. 8 (1991), 8-13), by highly parallel capilary electrophoresis (Huang et al., Anal. Chem. 64 (1992), 2149-2154; Kambara and Takahashi, Nature 361 (1993), 565-566), by oligonucleotide hybridization (Drmanac et al., Genomics 4 (1989), 114-128; Khrapko et al., FEBS Let. 256 (1989), 118-122; Maskos and Southern, Nucleic Acids Res. 20 (1992), 1675-1678 and 1679-1684) and by matrix-assisted laser desorption/ionization mass spectroscopy (Hillenkamp et al., Anal. Chem. 63 (1991), 1193A-1203A).

Another approach is single-molecule sequencing (Dörre et al., Bioimaging 5 (1997), 139-152), in which the sequence of nucleic acids is carried out by progressive enzymic degradation of fluorescently labelled single-stranded DNA molecules and by detection of the sequentially released monomeric molecules in a microstructure channel. This process has the advantage of only a single molecule of the target nucleic acid being sufficient for carrying out a sequence determination.

Although application of the above-mentioned methods has already resulted in considerable progress, there is a great need for further improvements. The object on which the present invention is based was therefore to provide a process for sequencing nucleic acids, which represents a further improvement compared to the prior art and which makes possible parallel determination of individual nucleic acid molecules in a multiplex format.

PCT/EP01/07462 proposes a multiplex sequencing process which comprises providing, in an immobilized form, nucleic acid molecules carrying a plurality of fluorescent labelling groups on a support and determining simultaneously the base sequence of a plurality of nucleic acid molecules on the basis of the time-dependent change, caused when nucleotide building blocks are cleaved off, in the fluorescence of said nucleic acid molecules or/and said cleaved-off nucleotide building blocks. According to WO2003/052137, the sequence is determined by irradiating light into the support and generating an evanescent excitation field by way of internal reflection on the support surface in the region of the immobilized nucleic acid molecules.

PCT/EP2005/008511 describes a multiplex sequencing process which comprises providing, in an immobilized form, nucleic acid-degrading and/or nucleic acid-synthesizing enzyme molecules, contacting the immobilized enzymes with free nucleic acid molecules and determining simultaneously the base sequence of a plurality of nucleic acid molecules on the basis of the time-dependent fluorescence change caused when nucleic acid building blocks are incorporated into and/or cleaved off from the nucleic acid molecules.

A problem associated with prior sequencing processes is a lack of accuracy.

Thus, it was an object of the present invention to provide a novel process for sequencing nucleic acids, which provides an increased accuracy by carrying out a sequencing procedure allowing multiple sequence determinations on a single nucleic acid template molecule.

The present invention relates to a process for sequencing an individual nucleic acid, comprising the following steps:
(a) providing a nucleic acid-synthesizing enzyme molecule, a circular nucleic acid template molecule, a primer annealed to said template, or capable of annealing to said template and fluorescence-labelled nucleotide building blocks,
(b) generating a nucleic acid molecule complementary to the sequence of the circular nucleic acid template having incorporated said nucleic building blocks in a primer elongation catalyzed by a nucleic acid-synthesizing enzyme molecule,
(c) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
(d) determining the base sequence of said circular nucleic acid template molecule on the basis of the time-dependent fluorescence change, caused when nucleotide building blocks are incorporated during primer elongation and/or cleaved off during nuclease digestion.

The process of the invention is a single molecule sequencing method, wherein the sequence of an individual circular nucleic acid template molecule is determined. Preferably, the process is a multiplex sequencing method, wherein the base sequence of a plurality of individual circular nucleic acid template molecules is determined.

According to the process of the invention, the base sequence of an individual circular nucleic acid template molecule may be determined in at least one cycle comprising nucleic acid elongation and subsequent nucleic acid digestion. Preferably, the base sequence is determined in at least two, e.g. 2, 3, 4, 5 or even more cycles, each comprising nucleic acid elongation and nucleic acid digestion.

Preferably, the process of the invention is a support-based method. In one embodiment, the nucleic acid synthesizing enzyme molecule is immobilized on a support. In another embodiment, the circular nucleic acid molecule is immobilized on a support.

In one embodiment, the present application relates to a process for sequencing an individual nucleic acid molecule, comprising the following steps:
(a) providing at least one nucleic acid-synthesizing enzyme molecule immobilized on a support, a circular nucleic acid template, a primer annealed to said template or capable of annealing to said nucleic acid template, and fluorescence-labelled nucleotide building blocks, (b) generating a nucleic acid molecule complementary to the sequence of the circular nucleic acid template molecule having incorporated said nucleotide building blocks in a primer elongation catalyzed by said immobilized nucleic acid-synthesizing enzyme molecule, (c) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and (d) determining the base sequence of said circular nucleic acid template molecule on the basis of the time-dependent fluorescence change, caused when nucleotide building blocks are incorporated during primer elongation and/or cleaved off during nuclease digestion.

In a further embodiment, the present application relates to a process for sequencing an individual nucleic acid, comprising the following steps:

(a) providing a nucleic acid-synthesizing enzyme, a circular nucleic acid template molecule immobilized on a support, a primer annealed to said template or capable of annealing to said nucleic acid template, and fluorescence-labelled nucleotide building blocks, (b) generating a nucleic acid molecule complementary to the sequence of said immobilized circular nucleic acid template having incorporated said nucleotide building blocks in a primer elongation catalyzed by said nucleic acid-synthesizing enzyme molecule, (c) contacting said generated nucleic acid molecule with a nucleic acid degrading enzyme molecule and cleaving off individual nucleotide building blocks from said generated nucleic acid molecule in a nuclease digestion catalyzed by said nucleic acid-degrading enzyme molecule, and (d) determining the base sequence of said nucleic acid template on the basis of the time-dependent fluorescence change, caused when nucleotide building blocks are incorporated during primer elongation and/or cleaved off during nuclease digestion.

Preferably, the process of the invention is a support-based multiplex sequencing method which enables a multiplicity of individual nucleic acid molecules to be sequenced. This is achieved by providing a reaction space comprising a circular nucleic acid template, a nucleic acid-degrading enzyme and a nucleic acid-synthesizing enzyme for determining in parallel time-dependent fluorescence change in a plurality of nucleic acid synthesis and/or degradation reactions. The process is preferably carried out in the form of a parallel high throughput single molecule analysis.

In a preferred embodiment, a support having a multiplicity of nucleic acid-synthesizing enzyme molecules immobilized thereon is provided. The support also may have immobilized thereon a multiplicity of nucleic acid-degrading enzyme molecules. In other embodiments, nucleic acid-degrading enzyme molecules are used in a free form. In still other embodiments, hybrids and/or conjugates of nucleic acid-synthesizing enzyme molecules and nucleic acid-degrading enzyme molecules, e.g. genetic fusions and/or conjugates linked by bi-functional linker molecules, are immobilized on the support.

In a further preferred embodiment, a support having a multiplicity of circular nucleic acid template molecules immobilized thereon is provided. In this embodiment, nucleic acid synthesizing enzyme molecules and nucleic acid-degrading enzyme molecules or hybrids and/or conjugates thereof are used in a free form.

The support used for said process may be any planar or structured support which is suitable for immobilizing enzyme molecules. Examples of suitable support materials are glass, quartz, plastic, metals, semimetals such as silicon, for example, metal oxides such as silicon dioxide, for example, or composites comprising said materials. Said support may, at least in the region of the immobilized enzyme or nucleic acid molecules, have sufficient optical transparency and suitable surface properties for irradiation with fluorescence excitation light or/and backscatter of fluorescence emission light through the support or for evanescence-based fluorescence detection. In principle, the support may also have any design, as long as a reaction space can be formed which enables individual nucleotide building blocks to be incorporated into and cleaved off progressively from the nucleic acids contacted with said support in a liquid reaction mixture.

The process of the present invention may be carried out in a single reaction space which is formed across the support or the portion thereof, on which the enzyme or nucleic acid molecules are immobilized. Alternatively, the process may also be carried out in a multiplicity of separate reaction spaces across the support, wherein the separate reaction spaces are not in communication with each other, at least during certain steps of the process. Multiple separate reaction spaces may e.g. be formed by nano- and/or microwells and/or nano- or microspots on the support.

The enzyme or nucleic acid molecules may bind to this support via covalent or noncovalent interactions. For example, high-affinity interactions between the partners of a specific binding pair, for example biotin/streptavidin or avidin, hapten/anti-hapten antibody, sugar/lectin, etc., can mediate binding of the polypeptides or nucleic acids to the support. Thus it is possible to couple biotinylated enzyme or nucleic acid molecules to streptavidin-coated supports. Alternatively, the enzyme or nucleic acid molecules may also be bound to the support via adsorption. Thus enzyme or nucleic acid molecules modified by incorporation of alkane thiol groups, may bind to metallic supports, e.g. supports made of gold. Yet another alternative is covalent immobilization in which it is possible to mediate enzyme or nucleic acid molecule binding via reactive silane groups on a silica surface.

In preferred embodiments, a plurality of nucleic acid-synthesizing enzyme molecules and optionally of nucleic acid-degrading enzyme molecules or a plurality of circular nucleic acid template molecules is bound to a single support. The molecules immobilized on the support and the sample liquid in contact therewith, which contains the free reaction partners, define one or more reaction spaces. Preferably at least 100, particularly preferably at least 1000, and particularly preferably at least 10 000, and up to more than $10^6$, enzyme or nucleic acid molecules are bound to said support. Preference is given to said enzyme or nucleic acid molecules binding to said support in such a way that a diluted molecule layer is produced on said support, preferably containing from 0.01 to 2, preferably 0.1 to 1, enzyme or nucleic acid molecules per $\mu m^2$ of support surface area.

The enzyme or nucleic acid molecules may be applied randomly, for example by contacting a diluted solution of biotinylated enzyme or nucleic acid molecules with a support two-dimensionally coated with streptavidin. Alternatively, the enzyme or nucleic acid molecules may also be bound to specific regions of the support surface, for example by contacting a diluted solution of biotinylated enzyme or nucleic acid molecules with a structured support, only particular regions of which are coated with streptavidin. In embodiments where the nucleic acid-degrading enzyme molecules are immobilized, they are preferably co-immobilized with nucleic acid-synthesizing molecules, i.e. both types of enzyme molecules are bound in the same specific regions of the support surface.

The nucleic acid template whose sequence is to be determined may be selected, for example, from DNA templates such as genomic DNA fragments, cDNA molecules, plasmids, etc., or else from RNA templates such as mRNA molecules. The template may originate from genomic or expression libraries, generated from cells or organisms, e.g. eukaryotic or prokaryotic cells or organisms. The process of the present invention allows parallel sequencing of a plurality of different nucleic acid template molecules, e.g. at least 10, 100, 1.000 or 10.000 and up to 100.000, $10^6$ or $10^7$ or even more different nucleic acid molecules.

Preferably, the nucleic acid molecules to be sequenced are single-stranded nucleic acid molecules in a circular form, more preferably a covalently linked circular form. In order to obtain a circular nucleic acid template, a linear nucleic acid molecule is subjected to a circularization procedure and optionally a strand-separation procedure during sample preparation. Circularization may be effected by ligation according to known protocols, e.g. using DNA or RNA ligases. In some embodiments, an adaptor and/or identifier molecule, i.e. a nucleic acid molecule of known sequence, may be coupled to the nucleic acid molecule before circularization. If necessary, nucleic acid strands may be separated before or after circularization, in order to obtain a singe-stranded template molecule.

The circular nucleic acid template molecules are preferably from 50 to 2000 nucleotides, particularly preferably from 200 to 1000 nucleotides, in length. Preferably, the nucleic acid template molecules to be sequenced do not contain fluorescent labelling groups.

The nucleic acid-synthesizing enzyme molecules are capable of elongating a primer annealed to a circular nucleic acid template molecule. Preferably, primer elongation is carried out by progressively incorporating individual nucleotide building blocks at the 3'-terminus of a growing nucleic acid chain, wherein a nucleic acid molecule complementary to the sequence of the circular nucleic acid template is generated. The nucleic acid-synthesizing enzymes are selected from polymerases capable of a template specific nucleic acid polymerization, preferably from DNA polymerases and RNA polymerases, e.g. natural or modified polymerases, including thermostable DNA polymerases.

The nucleic acid-degrading enzyme molecules are capable of progressively cleaving off individual nucleotide building blocks from a nucleic acid molecule. Preferably exonucleases, more preferably single-strand exonucleases which degrade in the 3'→5' direction or in the 5'→3' direction are used. Exonucleases which are particularly preferably used are 3'→5' exonucleases such as E. coli exonuclease I and E. coli exonuclease III, and 5'→3' exonucleases such as E. coli exonuclease II and E. coli exonuclease VIII.

The nucleic acid-synthesizing enzyme molecules are contacted with a circular nucleic acid template molecule, e.g. a single-stranded DNA or RNA molecule, and a primer molecule annealed to the circular nucleic acid template molecule or capable of annealing thereto. The primer molecule is preferably a single-stranded nucleic acid or nucleic acid analogue molecule having a free 3'-end which can be extended by an enzymatic reaction catalyzed by the immobilized nucleic acid-synthesizing enzyme molecules. The length of the primer molecule is selected to allow effective annealing to the template under reaction conditions. Usually, the length of the primer molecule is at least 8, at least 10, at least 12 or at least 15 nucleotides and e.g. up to 20, 25, 50 or 100 nucleotides, or even higher. In some embodiments, the primer is resistant against digestion by nucleic acid-degrading enzyme molecules, e.g. by incorporating nucleotide analogue building blocks and/or linkages between nucleotide building blocks, which are stable against degradation. In other embodiments, the primer is sensitive against digestion by nucleic acid-degrading enzyme molecules.

The sequence of the primer is selected in that it effectively anneals under reaction conditions to the template molecule. For instance, the primer may be a universal degenerated primer capable of statistically annealing to unknown nucleic acid sequences. In other embodiments, the primer may be capable of annealing to a known sequence portion of the circular nucleic acid template molecule. In this embodiment, a known adaptor and/or identifier sequence may be incorporated into the circular nucleic acid template molecule, e.g. during the circularization step as described above. The primer may be unlabelled or comprise fluorescent labelling groups.

Further, the presence of nucleotide building blocks carrying at least one fluorescent labelling group is required. Preferably, each different nucleotide building block (A, G, C, T/U) contains a different fluorescent labelling group.

The fluorescent labelling groups may be selected from known fluorescent labelling groups used for labelling biopolymers, particularly nucleic acids, such as, for example, fluoresceins, rhodamines, oxazines, for example Evoblue or Gnothis Blue, phycoerythrin, Cy3, Cy5, IR dyes or derivatives thereof, etc.

The nucleotide building blocks may carry (i) a fluorescence labelling group which remains with the building block when the building block is incorporated into a nucleic acid molecule during a primer elongation catalyzed by a nucleic acid-synthesizing enzyme molecule, and/or (ii) a fluorescence labelling group which is cleaved off from the building block when the building block is incorporated into a nucleic acid molecule during a primer elongation catalyzed by a nucleic acid-synthesizing enzyme molecule. Fluorescence labelling groups remaining with the building block are preferably attached to the α-phosphate group, to the sugar and/or to the nucleobase group. Preferably, fluorescence labelling groups remaining with the building block are attached to the nucleobase, e.g. via a linker which may have a chain-length of up to 15, preferably of 10-12 carbon atoms, optionally including hetero, e.g. N, O or S atoms. Fluorescence labelling groups which are cleaved off when the building block is incorporated into a nucleic acid molecule may be attached e.g. to the γ-phosphate group. In certain embodiments, building blocks are selected which contain both (i) a fluorescence labelling group remaining after incorporation and (ii) a fluorescence labelling group cleaved off during incorporation. In this case, fluorescence groups capable of interacting with each other, e.g. by quenching and/or energy transfer, may be selected.

The process of the present invention involves a first step of generating nucleic acid molecules having incorporated nucleotide building blocks in a primer elongation catalyzed by the nucleic acid-synthesizing enzyme molecules and a second step of cleaving off individual nucleotide building blocks from the generated nucleic acid molecules catalyzed by nucleic acid-degrading enzyme molecules. Dependent on the type of fluorescence labels, nucleic acid sequence determination may be carried out during the first step and/or during the second step.

Sequence determination during the first step (generation of a nucleic acid molecule) involves the use of nucleotide building blocks carrying a fluorescence-labelling group which is cleaved off from the building block when it is incorporated into a nucleic acid molecule. In this case, a time-dependent fluorescence change caused by cleaving off the fluorescence-labelling group from the nucleotide building block may be determined. Sequence determination in the second step involves the use of a nucleotide building block, which carries a fluorescence-labelling group which remains with the building block when it is incorporated into a nucleic acid molecule. Progressive cleavage of individual nucleotide building blocks from the nucleic acid molecules causes a time-dependent change of fluorescence when the labelled nucleotide building block is liberated from the nucleic acid molecule. In certain embodiments, it is also possible to carry out a sequence determination during the first and the second step, i.e. when using nucleotide building blocks, which both carry a fluorescence-labelling group remaining with the building block and a fluorescence-labelling group which is cleaved off from the building block when the building block is incorporated into a nucleic acid molecule. In this embodiment, both fluorescent groups may be the same or different.

The method of the invention involves at least one cycle of nucleic acid-synthesis and nucleic acid-degradation in order to determine the base sequence of the circular nucleic acid molecule template. The nucleic acid synthesis involves an elongation of the primer annealed to the circular nucleic acid template molecule catalyzed by the nucleic acid-synthesizing enzyme molecule, wherein a nucleic acid molecule complementary to the sequence of the circular nucleic acid template is generated. In the next step, the generated nucleic acid molecule is degraded by a nucleic acid-degrading enzyme molecule.

In some embodiments, the nucleic acid-degrading enzyme molecule degrades the generated nucleic acid molecule in 5'→3' direction, i.e. starting with the primer. In this embodiment, elongation and degradation may be performed in a "rolling circle", wherein elongation and subsequent degradation take place at least once or several times, e.g. 2, 3, 4 or 5 times around the circular template. In another embodiment a primer which is resistant against digestion by nucleic acid-degrading enzyme molecules may be used. In this embodiment, the nucleic acid molecules generated by primer elongation may be digested by a nucleic acid-degrading enzyme in 3'→5' direction until the resistant primer. The steps of generating nucleic acid molecules by primer elongation and subsequently digesting the generated nucleic acid molecules, can be repeated one or several, e.g. 2, 3, 4 or 5 times. Thus, in a preferred embodiment the sequence of a nucleic acid template molecule can be determined by several sequencing cycles, thereby increasing the accuracy of the obtained sequence information to a substantial extent.

The rates of primer elongation and nucleic acid degradation depend on several parameters, e.g. on the types of nucleic acid-synthesizing enzyme molecules and nucleic acid-degrading enzyme molecules, their relative amounts and the reaction conditions. Preferably, the reaction is carried out under conditions, wherein nucleic acid elongation initially occurs at a faster rate than nucleic acid degradation. In a later stage, the reaction conditions may be varied to increase the degradation rate, e.g. by reducing the concentration of available nucleotide building blocks.

When a nucleotide building block is incorporated into the elongated nucleic acid molecule, a time dependent change in the fluorescence may occur, which can be detected as indicated above. Preferably, the incorporation of the nucleotide building blocks into the elongated nucleic acid molecule is associated with a detectable increase in the fluorescence, preferably with a transient increase in the fluorescence. For example, nucleotide building blocks may be used which carry a fluorescent labelling group on the portion of the molecule which is cleaved off when the building block is incorporated into the primer, e.g. on the γ-phosphate group.

When a nucleotide building block is cleaved off from the synthesized nucleic acid molecule, a time-dependent change of fluorescence may be determined due to the interaction of fluorescent labelling groups incorporated in nucleic acid strands with neighbouring groups, for example with chemical groups of the nucleic acids, in particular nucleobases such as, for example, G, or/and neighbouring fluorescent labelling groups, and these interactions leading to a change in fluorescence, in particular in fluorescence intensity, compared to the fluorescent labelling groups in "isolated" form, owing to quenching processes or/and energy transfer processes. The removal by cleavage of individual nucleotide building blocks alters the overall fluorescence, for example the fluorescence intensity of an immobilized nucleic acid strand, and this change is a function of the removal by cleavage of individual nucleotide building blocks, i.e. a function of time.

This time-dependent change in fluorescence during elongation and/or degradation may be recorded in parallel for a multiplicity of nucleic acid molecules and correlated with the base sequence of the individual nucleic acid strands. Preference is given to using those fluorescent labelling groups which, when incorporated in the nucleic acid strand, are, at least partially, quenched so that the fluorescence intensity is increased after the nucleotide building block containing the labelling group or a neighbouring building block causing quenching has been removed by cleavage.

During incorporation and removal of individual nucleotide building blocks, it is possible to measure a change in fluorescence intensity of the nucleic acid strand or/and the incorporated or cleaved-off nucleotide building block, owing to quenching processes or energy transfer processes. This change in fluorescence intensity with time depends on the base sequence of the nucleic acid strand studied and can therefore be correlated with the sequence.

The complete sequence of the nucleic acid template may be determined by using a mixture of nucleotide building blocks, labelled on all four different bases, for example on A, G, C and T, or on combinations of two or three different bases. It is possible, where appropriate, to attach to the nucleic acid strand to be studied also a "sequence identifier", i.e. a labelled nucleic acid of known sequence, for example by enzymatic reaction using ligase or/and terminal transferase, so that at the start of sequencing initially a known fluorescence pattern and only thereafter the fluorescence pattern corresponding to the unknown sequence to be studied is obtained.

In a preferred embodiment of the present invention the cycle of synthesis and subsequent degradation can be repeated several times along the template. In each step of the cycle (synthesis or degradation or synthesis and degradation) sequence information with regard to the nucleic acid template molecule may be obtained. Repeating the cycles increases the content and quality of information by eliminating potential reading errors, which might occur in individual sequencing steps and/or sequencing cycles.

The detection comprises irradiating light into the support, preferably by means of a laser, or by another suitable light source, in order to cause excitation of the fluorescent labelling groups. It is possible, in this connection, to use one or more laser beams, for example an expanded laser beam, having a cross section of approx. 1-20 mm, or/and multiple laser beams. The detection preferably comprises a multipoint fluorescence excitation by lasers, for example a dot matrix of laser dots generated via diffraction optics (cf. WO 2002/097406) or a quantum well laser.

Alternatively, fluorescence may also be detected by irradiating light into the support and generating an evanescent excitation field by way of internal reflection at the support surface in the region of immobilized molecules. Internal reflection at one or more positions of the support surface in the region of immobilized enzyme molecules generates an evanescent excitation field which causes excitation of the fluorescent labelling groups of the nucleic acid molecules to be sequenced. Said reflection at the support surface is preferably total internal reflection.

Fluorescence emission of a plurality of nucleic acid strands may be detected in parallel using a detector matrix which comprises, for example, an electronic detector matrix, for example a CCD camera, a CMOS detector matrix, e.g. a CMOS camera, or an avalanche photodiode matrix. The detection may be carried out in such a way that fluorescence excitation and detection are carried out in parallel on all nucleic acid strands studied. A possible alternative to this is to study in several steps in each case a portion of the nucleic acid strands. Preference is given to carrying out the detection on fluorescence light which is emitted essentially orthogonally from the support surface through the reaction space or through the support body.

The detection may be carried out, for example, by means of confocal single molecule detection, for example by fluorescence correlation spectroscopy, which involves exposing a very small, preferably confocal, volume element, for example from $0.1 \times 10^{-15}$ to $20 \times 10^{-12}$ l, to the excitation light of a laser, or another suitable light source, which light excites the receptors present in this measuring volume so that the latter emit fluorescence light, the fluorescence light emitted from said measuring volume being measured by means of a photodetector and the change in the measured emission with time being correlated with the concentration of the analyte, so that it is possible to identify, at an appropriately high dilution, individual molecules in said measuring volume. Details of the procedure and of the apparatus used for detection can be found in the disclosure of the European patent 0 679 251. The confocal determination of single molecules is furthermore described in Rigler and Mets (Soc. Photo-Opt. Instrum. Eng. 1921 (1993), 239 ff.) and Mets and Rigler (J. Fluoresc. 4 (1994) 259-264).

Alternatively or additionally, detection may also be carried out by way of time-resolved decay measurement, called "time gating", as described, for example, by Rigler et al., "Picosecond Single Photon Fluorescence Spectroscopy of Nucleic Acids", in: "Ultrafast Phenomenes", D. H. Auston, Ed., Springer 1984. Here, the fluorescent molecules are excited in a measuring volume followed by, preferably at a time interval of ≥100 ps, opening a detection interval on the photodetector. In this way it is possible to keep background signals generated by Raman effects sufficiently low so as to enable single molecules to be detected in an essentially interference-free manner.

The invention further relates to an apparatus for sequencing an individual nucleic acid molecule or a plurality of individual nucleic acid molecules, comprising:

(a) a support,
(b) (i) a nucleic acid-synthesizing enzyme molecule,
   (ii) a circular nucleic acid template,
   (iii) a primer molecule which is annealed to or capable of annealing to the template,
   (iv) nucleotide building blocks carrying a fluorescent labelling group, and
   (v) a nucleic acid-degrading enzyme molecule,
(c) at least one reaction space on said support for elongating said primer by incorporating said nucleotide building blocks and for degrading said elongated primer by cleaving off said incorporated building blocks, and
(d) means for determining simultaneously the base sequence of said template on the basis of the time-dependent fluorescence change, caused when nucleotide building blocks are incorporated during a primer elongation and/or cleaved off during a nuclease digestion.

In some embodiments, the nucleic acid-synthesizing enzyme molecule is immobilized on the support and the circular nucleic acid template, the primer and the nucleotide building blocks are present in free form. The nucleic acid degrading enzyme may be present in immobilized or in free form. The reaction space is defined around the nucleic acid synthesizing enzyme molecule immobilized on the support.

In another embodiment, the circular nucleic acid template molecule is immobilized on the support. The nucleic acid synthesizing enzyme molecule, the nucleotide building blocks and the nucleic acid-degrading enzyme molecule are present in free form. The primer may be present in a form which is bound to the template molecule or in a form capable of binding to the template molecule.

The apparatus is preferably a micro- or nanoscale structure suitable for determining single molecules, for example an at least partially transparent structure having channels or/and depressions. A preferred nano structure is described in PCT/EP02/02582.

The process of the invention and the apparatus of the invention may be employed, for example, in the analysis of genomes and transcriptomes or in differential analyses, for example studies regarding the difference in the genome or transcriptome of individual species or organisms within a species.

In a preferred embodiment, the process of the invention and the apparatus of the invention may be employed in the analysis of quasi-species sequences (cf. M. Eigen et al., "Molecular Quasi Species", *J. Phys. Chem.* 92, December 1988, 6881-6891; M. Eigen & C. Biebricher, "Role of Genome Variation in Virus Evolution", in *RNA Genetics*, Vol. 3: Variability of RNA Genomes; CRC Press 1988; M. Eigen & R. Winkler-Oswatitsch, "Statistical Geometry on Sequence Space", in *Molecular Evolution: Computer Analysis of Protein and Nucleic Acid Sequences*, Academic Press, 1990, M. Eigen et al., "The Hypercycle-Coupling of RNA and Protein Biosynthesis in the Infection Cycle of an RNA Bacteriophage", *Biochemistry* 30, November 1991, 11005-11018, M. Eigen, "Viral Quasispecies", *Scientific American*, July 1993, 42-49, E. Domingo et al. "Quasispecies and RNA Virus Evolution: Principles and Consequences", *Landes Bioscience Madame Curie Database,* 2000 and references recited therein). By means of single molecule sequencing, the distribution of individual sequences within a population of organisms within a species or within a population of cells within an organism may be determined. For example, populations of organisms, such as bacteria or viruses, or populations of cells, such as spermatozoa, do not contain identical genetic information in certain sequences of their genomes. Instead, there are distinct individual sequences (corresponding to so-called quasi-species or sub-species) present, which differ in one or several, e.g. 2, 3 or 4 nucleotides, over a given length. The present invention now allows exact determination of individual variant sequences by means of single molecule sequencing, particularly by means of repeated cycles of single molecule sequencing of individual variants. Thereby, the frequency and distribution of individual sub-sequences within a population of organisms, e.g. viral or bacterial organisms, or a population of cells, e.g. spermatozoa, may be determined. By means of this information, the distribution of sub-species within a given population of organisms or a population of cells may be exactly determined. This allows—in case of pathogenic organisms such as bacteria or viruses—an improved diagnosis and therapy, e.g. by detecting the presence or absence of drug-resistant mutations. In case of cells such as spermatozoa, an improved genetic analysis, e.g. by detecting the presence or absence of certain genotypes, may be carried out.

Thus, further subject-matter of the invention is a process for determining the frequency and distribution of sub-sequences within a population of organisms or cells, comprising the following steps:
(a) providing a multiplicity of individual sub-sequences from a population of organisms or cells, e.g. at least 100, at least 1.000 or at least 10.000 individual sub-sequences, and
(b) determining the base-sequence of said individual sub-sequences by single molecule sequence analysis.

Particularly, the process is carried out according to the process as described above. Modifications of the process, however, may be possible, e.g. using linear nucleic acid templates, nucleic acid template molecules immobilized on the support and free nucleic acid synthesizing enzyme molecules.

Furthermore, the figures below are intended to illustrate the present invention.

FIG. 1 is a diagrammatic representation of a support (2) of the invention having a multiplicity of nucleic acid-synthesizing enzyme molecules (4*a*) immobilized thereon. A support having a surface area of from 1 to 2 $cm^2$ may contain up to $10^6$ enzyme molecules, for example.

Alternatively, the support may have a multiplicity of individual circular nucleic acid template molecules immobilized thereon. Preferably, the multiplicity of sequences defines a plurality of quasispecies sequences derived from a population of different organisms within a species.

Figure 2A:
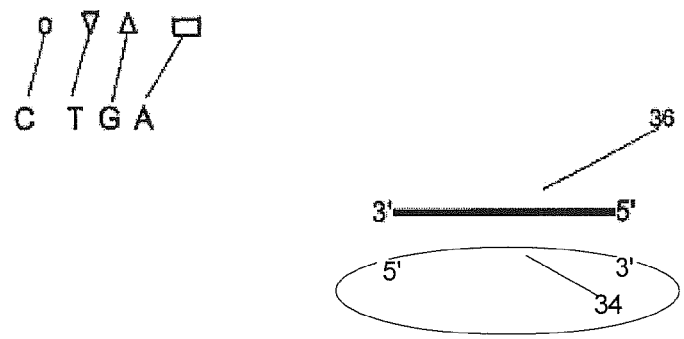
Figure 2A:
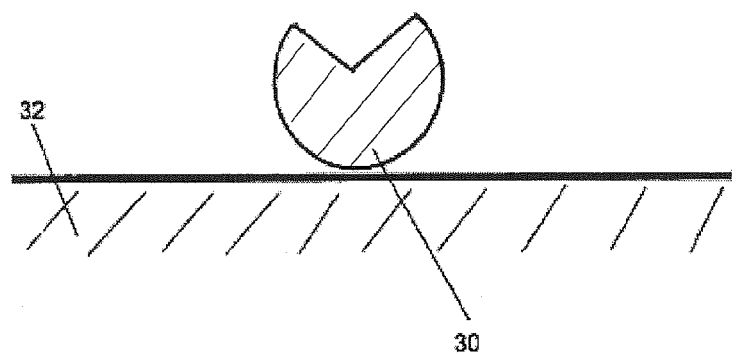

FIG. 2A shows the use of a nucleic acid-synthesizing enzyme molecule (30) immobilized on a solid support (32). The immobilized enzyme (30) is contacted with a single-stranded circular nucleic acid template molecule (34) to which a primer molecule (36) having a free 3'-end is annealed. Further, nucleotide building blocks (A, G, T, C) each carrying a different fluorescence labelling group a present. Primer extension by incorporating the nucleotide building blocks generates a time-dependant change in the fluorescence which can be detected.

In an alternative embodiment, the single-stranded circular nucleic acid template molecule may be immobilized on the solid support. The immobilized nucleic acid molecule having a primer molecule annealed thereto, is contacted with a free nucleic acid-synthesizing enzyme molecule in the presence of nucleotide building blocks in order to perform primer extension.

Figure 2B:
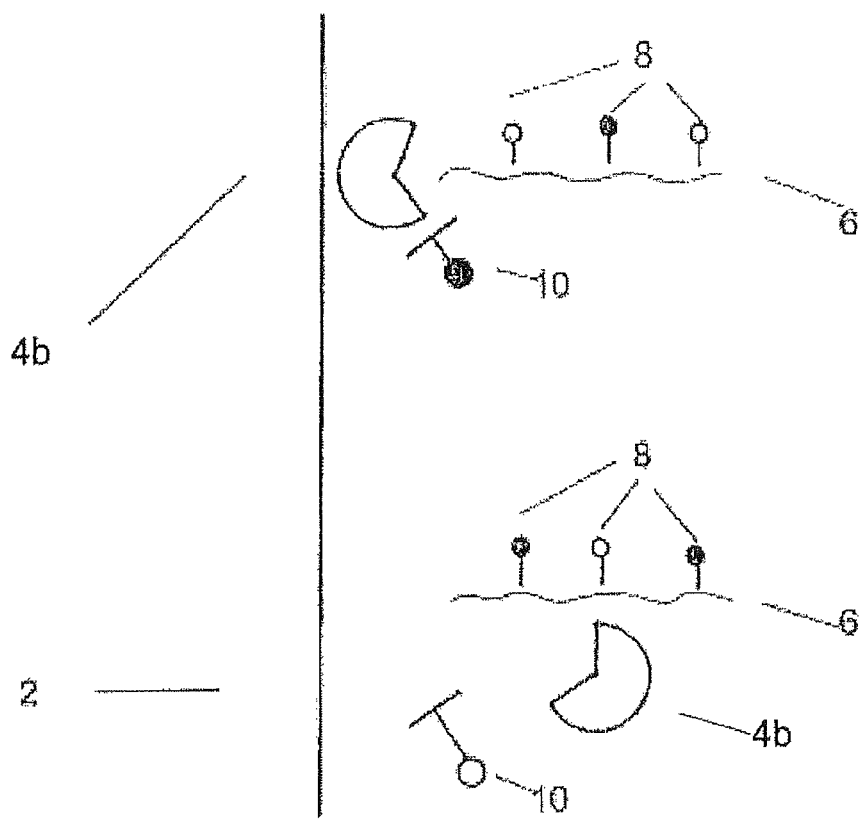

FIG. 2B depicts the subsequent degradation of the nucleic acid molecules synthesized according to FIG. 2A. The nucleic acid-degrading enzyme molecules (4*b*) may be immobilized on the support (2) (upper part) or present in fee form (lower part). They progressively cleave off individual nucleotide building blocks (10) from the elongated primer (6) having a plurality of fluorescent labelling groups (8). While the nucleotide building blocks incorporated into the nucleic acid strand exhibit only low fluorescence or no fluorescence at all, owing to quenching processes, said fluorescence increases after the removal by cleavage. Said increased fluorescence may be detected by means of a detector.

In an alternative embodiment, degradation of the nucleic acid molecules generated by primer extension may also be performed when an immobilized circular nucleic acid template molecule is used.

Figure 3:
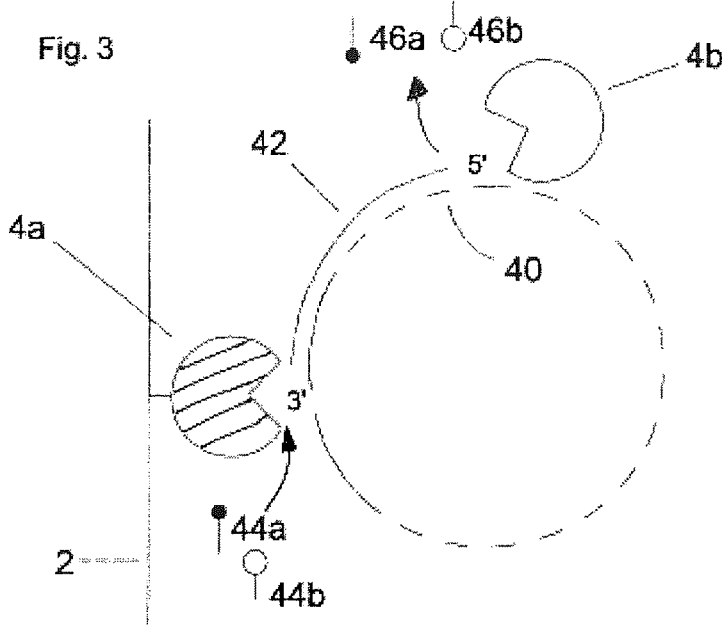

In FIG. 3 a preferred embodiment of the invention is shown. The nucleic acid-synthesizing enzyme molecule (4*a*) immobilized on the support (2) generates a nucleic acid molecule (42) complementary to the circular nucleic acid template molecule (40) by incorporating fluorescence-labelled nucleoside triphosphates (44*a*, 44*b*) at the 3'-end of the elongated nucleic acid molecule (42). A 5'→3' exonuclease (4*b*) digests the elongated nucleic acid molecule (42) from its 5' terminus thereby liberating fluorescence-labelled nucleoside monophosphates (46*a*, 46*b*). The elongation/digestion is carried out as a rolling circle, e.g. several times around the circular template.

In an alternative embodiment, elongation/digestion as a rolling cycle may also be performed on an immobilized circular nucleic acid template molecule.

Figure 4A:
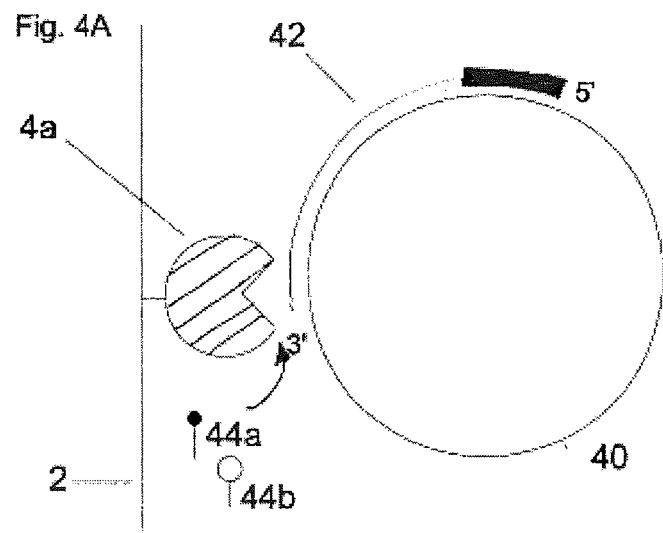
Figure 4B:
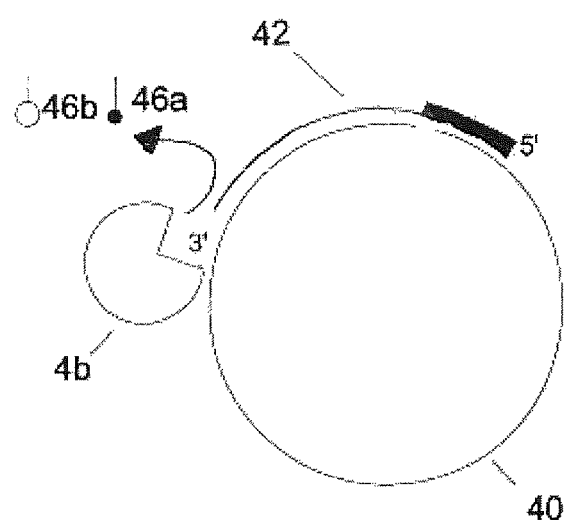

In FIGS. 4A and 4B a further preferred embodiment of the invention is shown. In FIG. 4A the nucleic acid-synthesizing enzyme (4*a*) immobilized on the support (2) generates an elongated nucleic acid molecule (42) complementary to the circular template (40) by incorporating fluorescence-labelled nucleoside triphosphates (44*a*, 44*b*) at the 3'-end of nucleic acid molecule (42). In this embodiment, nucleic acid molecule (42) has been generated by elongation of a degradation-resistant primer at its 5' end (shown on bold). In FIG. 4B the elongated nucleic acid molecule (42) is digested from its 3'-end by a 3'→5' exonuclease (4*b*) whereby fluorescence-labelled nucleoside monophosphates (46*a*, 46*b*) are progressively cleaved off.

In an alternative embodiment, the elongation/digestion process using a degradation-resistant primer may also be performed with an immobilized circular nucleic acid template molecule.

In an alternative embodiment, the elongation/digestion process using a degradation-resistant primer may also be performed with an immobilized circular nucleic acid template molecule.

Figure 5A:
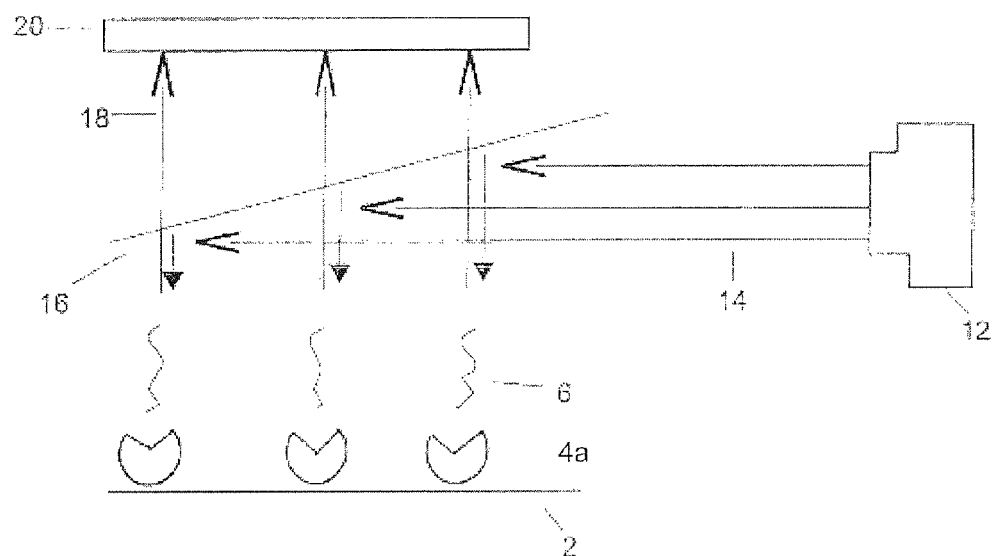

FIG. 5A depicts a first embodiment of a detection procedure. A support (2) having immobilized nucleic acid-synthesizing enzyme molecules (4*a*) thereon defines a reaction space comprising a sample fluid with nucleic acid molecules (6) undergoing an elongation and/or degradation process. A laser (12) irradiates excitation light (14) through the sample fluid. Said excitation light (14) may be directed, for example by a diffraction-optical element (16), confocally to the positions of the individual immobilized enzyme molecules. The fluorescence emission light (18) emitted by the sample fluid is recorded by a detector matrix (20), for example a CCD or a CMOS camera, in particular a matrix avalanche diode (SPAD) camera.

Figure 5B:
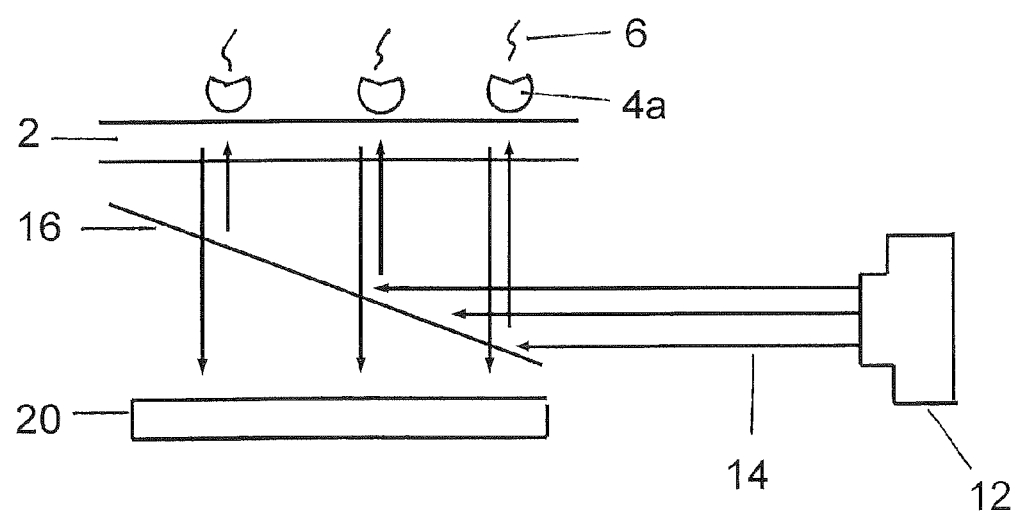

The embodiment depicted in FIG. 5B involves the nucleic acid molecules (6) being irradiated with excitation light (14), originating from the laser (12), through an optically transparent support (2). The emission light (18) which is likewise emitted through the support (2) is recorded by the detector matrix (20).

Figure 6:
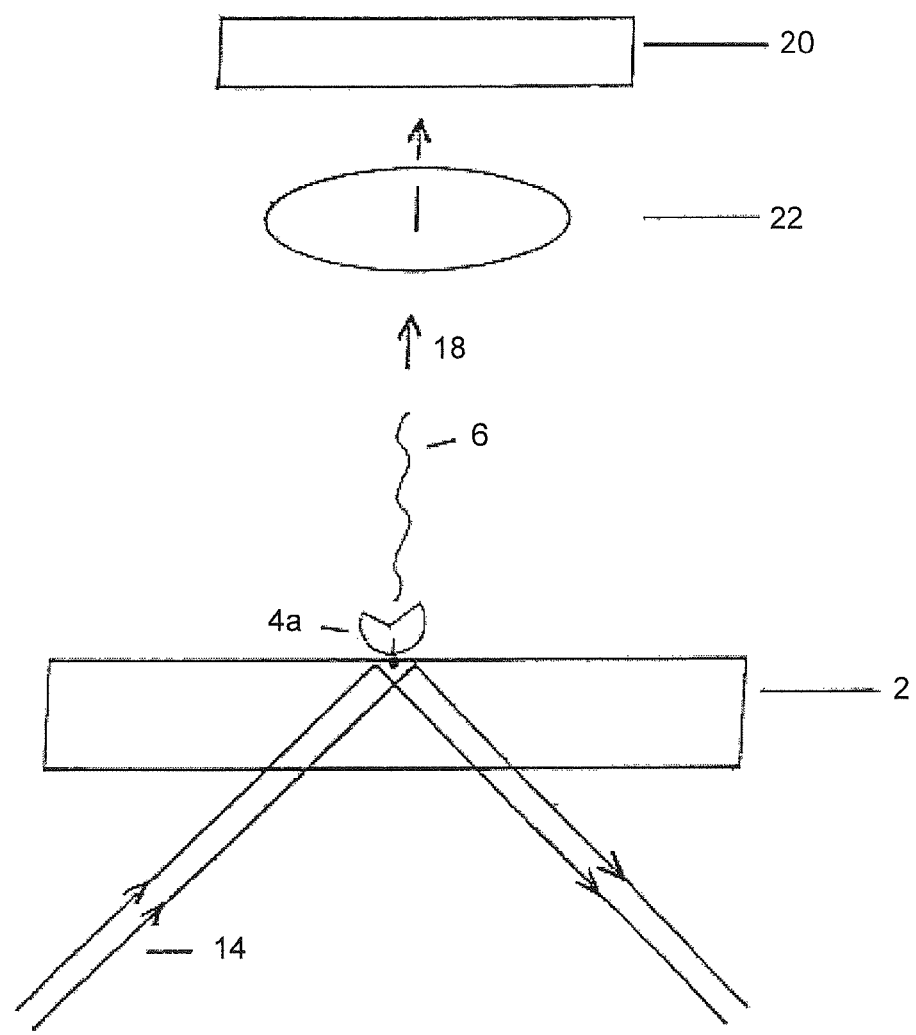

FIG. 6 depicts a further embodiment of the invention, wherein excitation light (14) from a laser is irradiated into an optically transparent support (2) having nucleic acid-generating enzyme molecules (4a) immobilized thereon and nucleic acid molecules (6) to be sequenced in close proximity thereto. The light (14) leaves the support (2) again after refraction at the support surface in the region of the immobilized enzyme molecules (4a). In this manner, an evanescent excitation field is generated by which the fluorescently labelled nucleic acid molecules or nucleotide building blocks are excited and fluoresce. The emission light (18) is directed through an optical element (22) to a detector (20), which may be located on the distal side of the substrate (2) with regard to the incident light (14) as shown in FIG. 6, and/or on the proximal side of the substrate (2) with regard to the incident light (14). In some embodiments, detection on the proximal side of the substrate (2) is preferred.

The irradiation/detection procedures shown in FIGS. 5A, 5B and 6 may also be performed in embodiments, wherein an immobilized circular nucleic acid template molecule is used.

Figure 7:
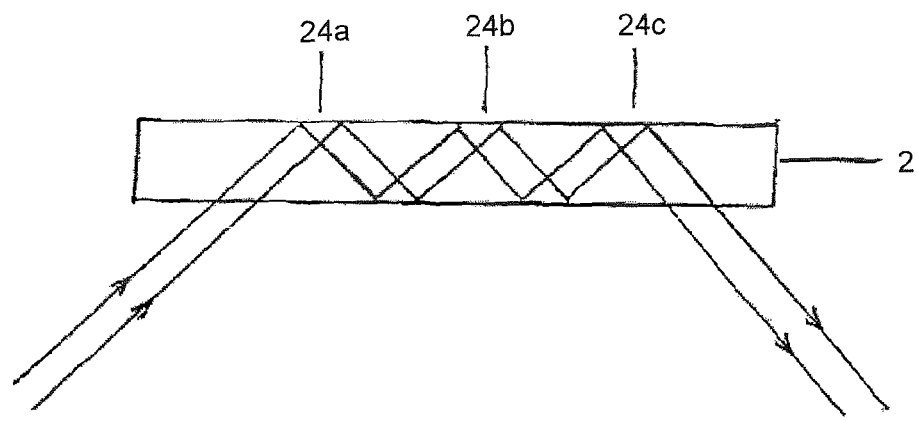

The embodiment depicted in FIG. 7 involves multiple refractions (24a, 24b, 24c) generating evanescent excitation fields in the optically transparent support (2). The evanescent excitation fields may be strip- or point-shaped, for example.

Alternatively, it is also possible to irradiate a plurality of laser light foci upon or into the support by using a diffractive optical element, as disclosed, for example, in DE 101 26 083.0.

Figure 8A:
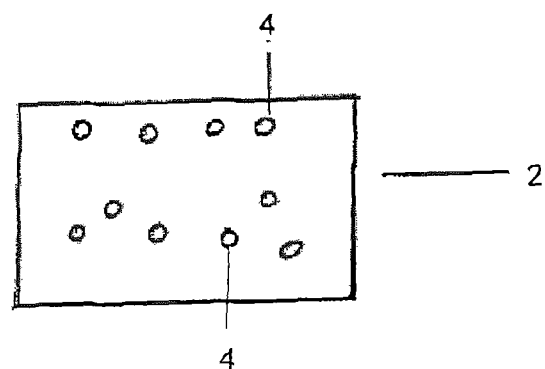
Figure 8B:
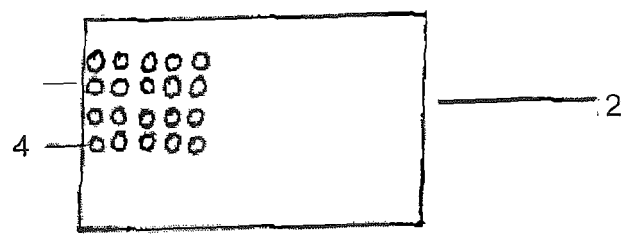

As shown in FIG. 8, the enzyme or nucleic acid molecules (4) immobilized on the support (2) may be arranged in a random or disordered manner on the support surface (FIG. 8A) or may be present in an ordered manner or on predefined structural areas (FIG. 8B).

The invention claimed is:

1. A process for sequencing an individual nucleic acid, comprising the following steps:
    (a) providing a nucleic acid-synthesizing enzyme molecule, a circular nucleic acid template molecule, a primer annealed to said template, or capable of annealing to said template and fluorescence-labelled nucleotide building blocks,
    (b) generating a nucleic acid molecule complementary to the sequence of the circular nucleic acid template having incorporated said nucleic building blocks in a primer elongation catalyzed by a nucleic acid-synthesizing enzyme molecule,
    (c) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
    (d) determining the base sequence of said circular nucleic acid template molecule on the basis of the time-dependent fluorescence change during building block cleavage and optionally incorporation, caused when nucleotide building blocks are incorporated during primer elongation and/or cleaved off during nuclease digestion,
    wherein the nucleic acid-synthesizing enzyme molecule is directly immobilized on a support, and
    wherein the nucleic acid-degrading enzyme molecule is present in free form.

2. The process of claim 1, wherein the base sequence of a plurality of individual circular nucleic acid template molecules is determined.

3. The process of claim 1, wherein the base sequence of an individual circular nucleic acid template molecule is determined at least in 2 cycles, each comprising elongation and digestion.

4. The process for sequencing an individual nucleic acid molecule according to claim 1, comprising the following steps:
    (a) providing at least one nucleic acid-synthesizing enzyme molecule immobilized on a support, a circular nucleic acid template molecule, a primer annealed to said template or capable of annealing to said nucleic acid template molecule, and fluorescence-labelled nucleotide building blocks,
    (b) generating a nucleic acid molecule complementary to the sequence of the circular nucleic acid template having incorporated said nucleotide building blocks in a primer elongation catalyzed by said immobilized nucleic acid-synthesizing enzyme molecule,
    (c) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
    (d) determining the base sequence of said circular nucleic acid template molecule on the basis of the time-dependent fluorescence change, caused when nucleotide building blocks are incorporated during primer elongation and/or cleaved off during nuclease digestion.

5. The process as claimed in claim 1, wherein a support made of glass, plastics, quartz, metals, semimetals, metal oxides or of a composite comprising a plurality of said materials is used.

6. The process as claimed in claim 1, wherein the nucleic acid-degrading enzyme molecule is an exonuclease.

7. The process as claimed in claim 6, wherein E. coli exonuclease I, E. coli exonuclease II, E. coli exonuclease III or E. coli exonuclease VIII is used.

8. The process as claimed in claim 1, wherein the nucleic acid-synthesizing molecule is selected from DNA or RNA polymerases.

9. The process as claimed in claim 1, wherein a plurality of enzyme molecules is immobilized on the support in a disordered or random manner.

10. The process as claimed in claim 1, wherein a plurality of enzyme molecules is immobilized on predefined regions of the support in an ordered manner.

11. The process as claimed in claim 1, wherein the nucleotide building blocks carry (i) a fluorescence-labelling group which remains with the building block, wherein the building block is incorporated into a nucleic acid molecule by a nucleic acid-synthesizing enzyme molecule, and/or (ii) a fluorescence-labelling group which is cleaved off from the building block, when the building block is incorporated into a nucleic acid molecule by a nucleic acid-synthesizing enzyme molecule.

12. The process as claimed in claim 11, wherein the nucleotide building blocks carry (i) a fluorescence-labelling group which remains with the building block, when the building block is incorporated into a nucleic acid molecule by a nucleic acid-synthesizing enzyme molecule.

13. A process as claimed in claim 11, wherein the nucleotide building blocks carry (ii) a fluorescence-labelling group which is cleaved off from the building block, when the building block is incorporated into a nucleic acid molecule by a nucleic acid-synthesizing enzyme molecule.

14. The process as claimed in claim 1, wherein determining the base sequence comprises fluorescence excitation, and/or the use of diffraction optics.

15. The process as claimed in claim 14, wherein the nucleic acid molecules to be sequenced are irradiated through the reaction space with laser light, and wherein fluorescence emission light emitted through the reaction space is determined.

16. The process as claimed in claim 14, wherein the nucleic acid molecules to be sequenced are irradiated with laser light through an at least partially optically transparent support, and wherein fluorescence emission light emitted through the support is determined.

17. The process as claimed in claim 16, wherein laser light is irradiated into the support and the formation of an evanescent excitation field is caused by internal reflection on the support surface in the region of immobilized molecules.

18. The process as claimed in claim 1, wherein determining the base sequence comprises detecting the fluorescence emission of a plurality of nucleic acid strands by means of a detection matrix.

19. The process as claimed in claim 18, wherein the detection matrix used is a CMOS camera, a CCD camera or an avalanche photodiode matrix.

20. The process as claimed in claim 1, wherein detection of the time-dependent fluorescent change is carried out by fluorescence correlation spectroscopy and/or time-resolved decay measurement.

21. The process as claimed in claim 1, wherein fluorescence excitation and fluorescence detection are carried out in parallel on all nucleic acid strands studied, or in several steps, in each case on a portion of the nucleic acid strands studied.

22. The process as claimed in claim 1, wherein a convection flow away from the support is generated during the determination.

23. The process as claimed claim 1, wherein the fluorescent labelling groups are, at least partially, quenched when incorporated into the nucleic acid strands and the fluorescence intensity is increased after removal by cleavage.

24. The method according to claim 6, wherein the exonuclease is a single-strand 5'→3' exonuclease or a single-strand 3'→5' exonuclease.

25. The process according to claim 14, wherein said fluorescence excitation is a multipoint fluorescence excitation by a laser or another suitable light source.

26. The process of claim 1, wherein immobilization on the support is performed via covalent immobilization by reactive silane groups on a silica surface or via noncovalent interactions selected from high-affinity interactions between partners selected from the group consisting of biotin/streptavidin or avidin, hapten/anti-hapten antibody, sugar/lectin, or adsorption to metallic supports by incorporation of alkane thiol groups into the nucleic-acid synthesizing enzyme to be immobilized on the support.

27. The process of claim 1, wherein the time-dependent fluorescence change occurs during both building block cleavage and incorporation.

28. A process for sequencing an individual nucleic acid in a multiplex format, comprising the following steps:
(a) providing a nucleic acid-synthesizing enzyme molecule, a circular nucleic acid template molecule, a primer annealed to said template, or capable of annealing to said template and fluorescence-labelled nucleotide building blocks,
(b) generating a nucleic acid molecule complementary to the sequence of the circular nucleic acid template having incorporated said nucleic building blocks in a primer elongation catalyzed by a nucleic acid-synthesizing enzyme molecule,
(c) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
(d) determining the base sequence of said circular nucleic acid template molecule on the basis of the time-dependent fluorescence change during building block cleavage and optionally incorporation, caused when nucleotide building blocks are incorporated during primer elongation and/or cleaved off during nuclease digestion,
wherein a multiplicity of the nucleic acid-synthesizing enzyme molecule is directly immobilized on a support in a single reaction space, and
wherein the nucleic acid-degrading enzyme molecule is present in free form.

29. A process for determining the frequency and distribution of individual sequence variants within a population of organisms or cells, comprising the following steps:
(a) providing a multiplicity of individual sub-sequences from a population of organisms or cells,
(b) determining the base-sequence of said individual sub-sequences by single molecule sequence analysis according to the following process:
(i) providing a nucleic acid-synthesizing enzyme molecule, a circular nucleic acid template molecule, a primer annealed to said template, or capable of annealing to said template and fluorescence-labelled nucleotide building blocks,
(ii) generating a nucleic acid molecule complementary to the sequence of the circular nucleic acid template having incorporated said nucleic building blocks in a primer elongation catalyzed by a nucleic acid-synthesizing enzyme molecule,
(iii) contacting said generated nucleic acid molecule with a nucleic acid-degrading enzyme molecule and cleaving off individual nucleotide building blocks from said generated nucleic acid molecule in a nuclease digestion catalyzed by said nucleic acid-degrading enzyme molecule, and
(iv) determining the base sequence of said circular nucleic acid template molecule on the basis of the time-dependent fluorescence change during building block cleavage and optionally incorporation, caused when nucleotide building blocks are incorporated during primer elongation and/or cleaved off during nuclease digestion,
wherein a multiplicity of the nucleic acid-synthesizing enzyme molecule is directly immobilized on a support in a single reaction space, and
wherein the nucleic acid-degrading enzyme molecule is present in free form.

30. The process according to claim 29, wherein said population of organisms or cells is at least 100 individual sequence variants.

31. The process according to claim 30, wherein said population of organisms or cells is at least 1000 individual sequence variants.

32. The process according to claim 31, wherein said population of organisms or cells is at least 10,000 individual sequence variants.

33. The process according to claim 29, wherein the base sequence of said circular nucleic acid template molecule is determined on the basis of the time-dependent fluorescence change during building block cleavage and incorporation, caused when nucleotide building blocks are incorporated during primer elongation and cleaved off during nuclease digestion.

* * * * *